United States Patent
Cho

(10) Patent No.: US 9,131,912 B2
(45) Date of Patent: Sep. 15, 2015

(54) DUAL-ENERGY X-RAY IMAGING SYSTEM AND CONTROL METHOD FOR THE SAME

(75) Inventor: Min Kook Cho, Gyeonggi-do (KR)

(73) Assignee: Samsung Electronics Co., Ltd., Yeongtong-gu, Suwon-si, Gyeonggi-do (KR)

(*) Notice: Subject to any disclaimer, the term of this patent is extended or adjusted under 35 U.S.C. 154(b) by 554 days.

(21) Appl. No.: 13/548,555

(22) Filed: Jul. 13, 2012

(65) Prior Publication Data

US 2013/0022170 A1      Jan. 24, 2013

(30) Foreign Application Priority Data

Jul. 20, 2011    (KR) .................. 10-2011-0071756

(51) Int. Cl.
*A61B 6/00*    (2006.01)

(52) U.S. Cl.
CPC ............. *A61B 6/482* (2013.01); *A61B 6/545* (2013.01)

(58) Field of Classification Search
USPC ................................... 378/62, 5, 19
See application file for complete search history.

(56) References Cited

U.S. PATENT DOCUMENTS

| | | | | |
|---|---|---|---|---|
| 4,780,897 A | * | 10/1988 | McDaniel et al. | 378/62 |
| 6,393,097 B1 | * | 5/2002 | Aufrichtig et al. | 378/98.11 |
| 2002/0075997 A1 | * | 6/2002 | Unger et al. | 378/98.9 |
| 2007/0196007 A1 | * | 8/2007 | Chen et al. | 382/131 |
| 2007/0217573 A1 | | 9/2007 | Bernhardt | |
| 2012/0063662 A1 | | 3/2012 | Kwon et al. | |

FOREIGN PATENT DOCUMENTS

| | | |
|---|---|---|
| EP | 1 216 661 A2 | 6/2002 |
| JP | 2002-330954 A | 11/2002 |
| WO | 2007/100550 A2 | 9/2007 |

* cited by examiner

*Primary Examiner* — Kiet T Nguyen
(74) *Attorney, Agent, or Firm* — Cha & Reiter, LLC

(57) ABSTRACT

A dual-energy X-ray imaging apparatus and a method obtain dual-energy X-ray images by sequentially radiating an X-ray of a first energy and a X-ray of a second energy to an object, with the intensity and the quantity of the second energy adjusted using brightness information of the first energy X-ray image for the object so that a precise X-ray image representing the characteristics of the object is obtained and a precise diagnosis is achieved.

20 Claims, 15 Drawing Sheets

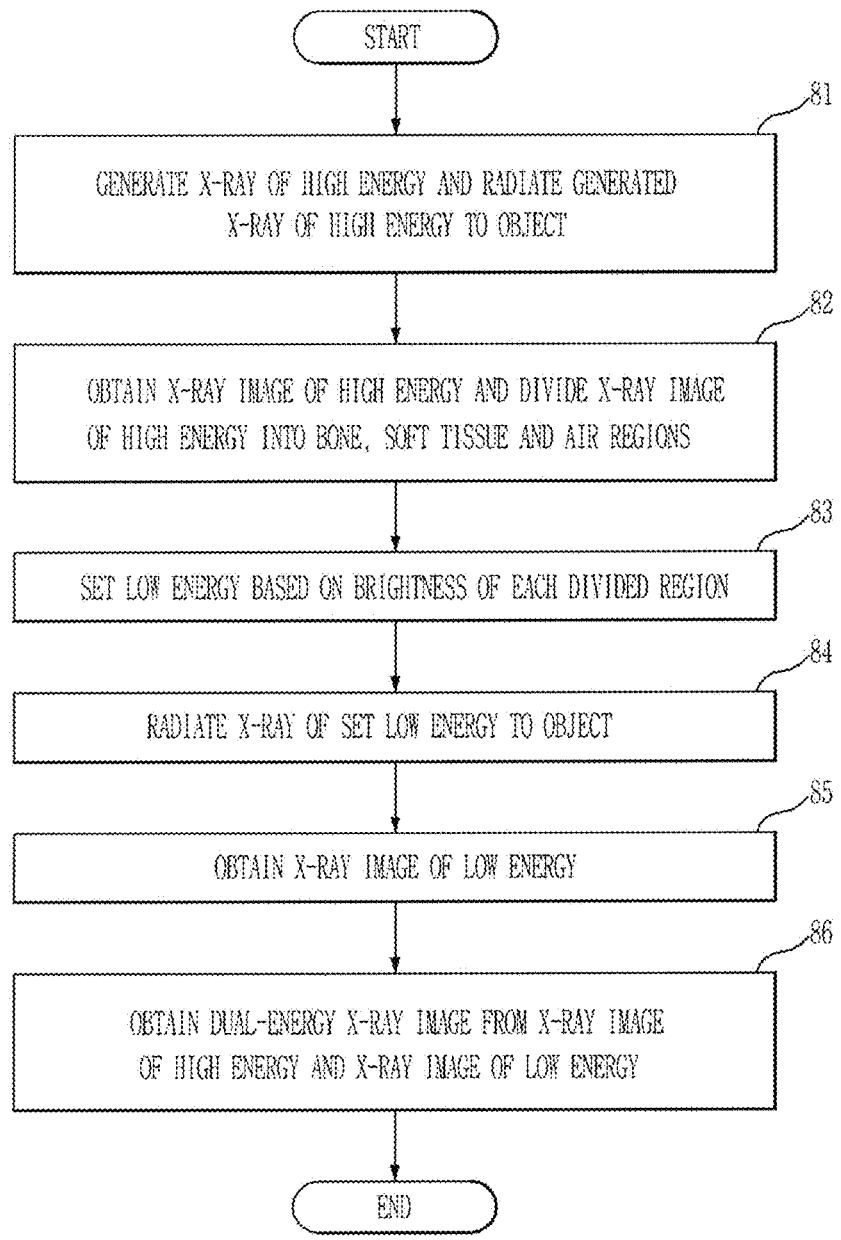

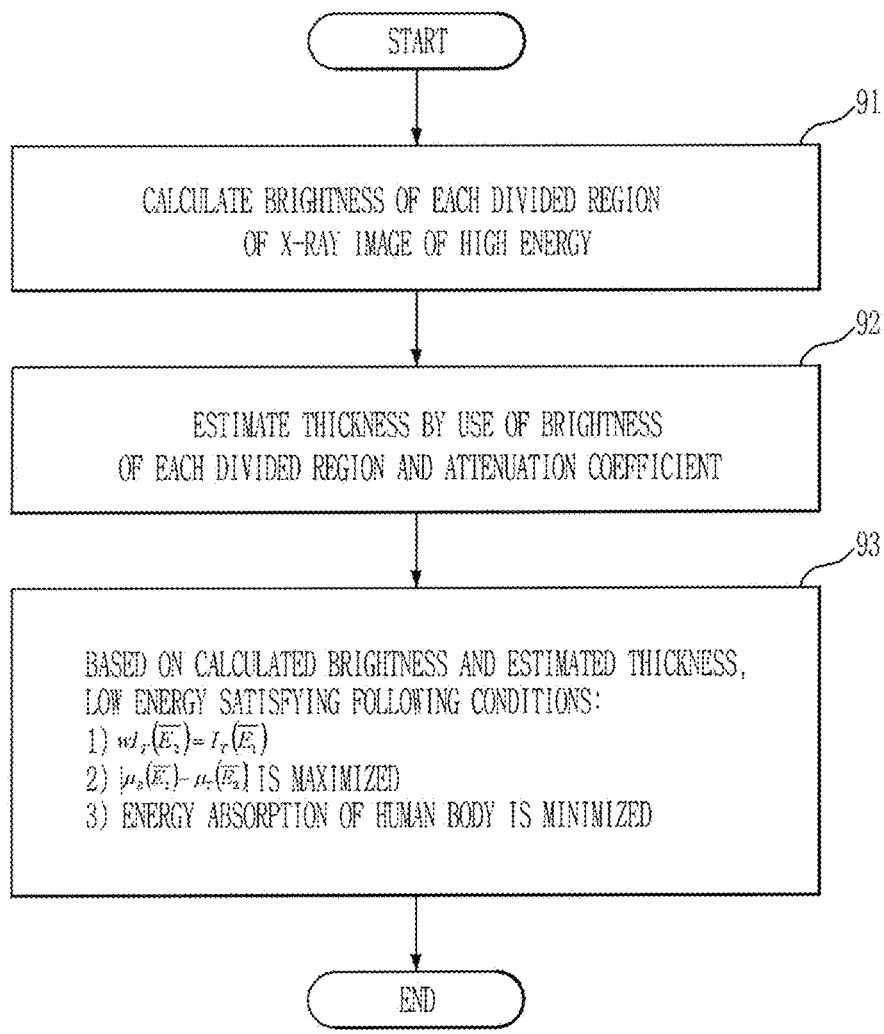

DUAL-ENERGY X-RAY IMAGING SYSTEM AND CONTROL METHOD FOR THE SAME

CLAIM OF PRIORITY

This application claims, pursuant to 35 U.S.C. §119(a), priority to and the benefit of the earlier filing date of Korean Patent Application No. 2011-0071756, filed on Jul. 20, 2011 in the Korean Intellectual Property Office, the disclosure of which is incorporated herein by reference.

BACKGROUND OF THE INVENTION

1. Field of the Invention

The present invention relates to a dual-energy X-ray imaging apparatus for obtaining an X-ray transmission image of an object by use of a high energy X-ray and a low energy X-ray.

2. Description of the Related Art

An X-ray imaging apparatus is an apparatus configured to obtain images of the inner structure of an object by radiating an X-ray to the object and by analyzing the X-ray passing through the object. Since the X-ray transmission is different for each tissue of the object, the inner structure of the object can be imaged by use of an attenuation coefficient that is obtained by quantifying the X-ray transmission.

In recent years, a dual-energy X-ray imaging technology that uses dual X-rays of a high energy and a low energy, instead of just a single-energy X-ray, has been developed, and many studies have been undertaken regarding such dual-energy X-ray imaging.

According to the dual-energy X-ray imaging technology, X-rays of a first energy and a second energy are sequentially radiated to an object to obtain a plurality of transmission images, and images of a bone and a soft tissue are separated from the obtained transmission images, so that a clear X-ray image is obtained. The intensity and the amount of X-ray energy to be transmitted are determined by the voltage and the electric current applied to the X-ray generating unit. The voltage and the electric current are set in advance for each portion of the object to be photographed.

However, if the intensity and the amount of X-ray energy are adjusted based on the set voltage and the electric current, the characteristics of the object are not considered, and thus presenting a limitation in the prior art dual-energy X-ray systems in adjusting the intensity and the amount of X-ray energy properly.

SUMMARY OF THE INVENTION

Therefore, it is an aspect of the present invention to provide a dual-energy X-ray imaging apparatus and a method of controlling the same, in which when dual-energy X-ray images are obtained by sequentially radiating an X-ray of a first energy and a X-ray of a second energy to an object, the intensity and the quantity of the second energy are adjusted by use of brightness information of the first energy X-ray image for the object so that a precise X-ray image representing the characteristics of the object is obtained and a precise diagnosis is achieved.

Additional aspects of the present invention will be set forth in part in the description which follows and, in part, will be obvious from the description, or may be learned by practice of the present invention.

In accordance with one aspect of the present invention, a dual-energy X-ray imaging apparatus includes an X-ray generating unit, a power supply unit, a detector unit and a host computer. The X-ray generating unit is configured to sequentially radiate an X-ray of a first energy and an X-ray of a second energy to an object. The power supply unit is configured to supply power to the X-ray generating unit. The detector unit is configured to detect the X-rays of the first and second energies, which are radiated from the X-ray generating unit and which pass through the object, and to convert the detected X-rays into corresponding electric signals. The host computer is configured to receive the electric signals such that an X-ray image of the first energy is obtained and to set the second energy by use of the brightness of the X-ray image of the first energy.

The dual-energy X-ray imaging apparatus further includes an image processing unit configured to obtain the X-ray image of the first energy and to divide the X-image of the first energy into a bone region, a soft tissue region, and an air region for each of a bone, a soft tissue, and air, respectively, through an image segmentation method.

The dual-energy X-ray imaging apparatus further includes an energy-setting unit configured to set the second energy of the second X-ray such that the brightness of the soft tissue region of the X-ray image of the first energy is identical to the brightness of a soft tissue region of the X-ray image of the second energy by use of the brightness of each of the divided regions.

The energy-setting unit is configured to set the second energy, which maximizes a difference in an attenuation coefficient between the bone and the soft tissue and minimizes energy absorption of the soft tissue.

The energy-setting unit is configured to set the second energy, which satisfies the energy setting equation described below, maximizes a difference in an attenuation coefficient between the bone and the soft tissue, and minimizes energy absorption of the soft tissue, such that $$wI_T(\overline{E_2}) = I_T(\overline{E_2}) \rightarrow wI_A e^{-\mu T(\overline{E_2}) T_T} = I_T(\overline{E_1}),$$

in which w represents a weight of the output of the power supply unit, $I_T(\overline{E_1})$ represents the brightness of the soft tissue region of the X-ray image of the first energy, $I_T(\overline{E_2})$ represents the brightness of the soft tissue region of the X-ray image of the second energy, $\overline{E_1}$ represents an average energy of a spectrum of the first energy, and $\overline{E_2}$ represents an average energy of a spectrum the second energy. Other parameters of the equation are described herein.

The image processing unit obtains a dual-energy image by obtaining the X-ray image of the first energy and the X-ray image of the second energy, and by removing an X-ray absorption effect for the bone or an X-ray absorption effect for the soft tissue from the X-ray image of the first energy and the X-ray image of the second energy using a difference in an attenuation characteristic of X-rays between a bone and soft tissue.

In accordance with one aspect of the present invention, a method of controlling a dual-energy X-ray imaging apparatus is as follows. An X-ray of a first energy, which is designated in advance, is radiated to an object. The X-ray of the first energy, which has passed through the object, is converted into an electric signal. An X-ray image of the first energy is obtained by use of the electric signal. A second energy is set using the brightness of the obtained X-ray image of the first energy. An X-ray image of the second energy is obtained by radiating an X-ray of the set second energy to the object. A dual-energy X-ray image is obtained from the obtained X-ray image of the first energy and from the obtained X-ray image of the second image.

In an exemplary embodiment, the first energy is a high energy and the second energy is a low energy.

The method further includes performing image segmentation by dividing the obtained X-ray image of the first energy into a bone region, a soft tissue region, and an air region for a bone, a soft tissue, and air, respectively.

The setting of the second energy is performed as follows. First, the brightness of each of the divided regions is calculated. Thicknesses of the bone and the soft tissue are calculated using the calculated brightness values and an attenuation coefficient of each of the bone and the soft tissue. Thereafter, the calculated brightness and the estimated thickness are used.

Using the calculated brightness and the estimated thickness, the present invention determines the second energy, which matches the brightness of the soft tissue of the X-ray image of the first energy to brightness of a soft tissue of the X-ray image of the second energy, maximizes a difference in an attenuation coefficient between the bone and the soft tissue, and minimizes energy absorption of the soft tissue.

Using the calculated brightness and the estimated thickness, the present invention determines the second energy, which satisfies the energy setting equation described below, maximizes a difference in an attenuation coefficient between the bone and the soft tissue, and minimizes energy absorption of the soft tissue at the second energy, such that $$wI_T(\overline{E_2}) = I_T(\overline{E_1}) \rightarrow wI_A e^{-\mu T(\overline{E_2})T_T} - I_T(\overline{E_1}),$$

in which, w represents a weight of output of the power supply unit, $I_T(\overline{E_1})$ represents the brightness of the soft tissue region of the X-ray image of the first energy, $I_T(\overline{E_2})$ represents the brightness of the soft tissue region of the X-ray image of the second energy, $\overline{E_1}$ represent an average energy of a spectrum of the first energy, and $\overline{E_2}$ represents an average energy of a spectrum the second energy. Other parameters of the equation are described herein.

By obtaining the dual-energy X-ray image, the present invention removes an X-ray absorption effect of the bone or the soft tissue from the X-ray image of the first energy and the X-ray image of the second energy using a difference in an attenuation characteristic of X-rays between the bone and the soft tissue.

According to the dual-energy X-ray imaging apparatus of the present invention and the control method for the same, the second energy is set based on the first energy X-ray image for the object, thereby obtaining a dual-energy X-ray image of clear image quality representing the characteristics of the object and thus providing a precise diagnosis.

In addition, the second energy enables the absorption of X-rays by the soft tissue to be minimized, so that the exposure dose is reduced during the X-ray photography, thereby enhancing the safety in use of X-rays by X-ray photography.

BRIEF DESCRIPTION OF THE DRAWINGS

These and other aspects of the present invention will become apparent and more readily appreciated from the following description of the exemplary embodiments of the present invention, taken in conjunction with the accompanying drawings of which:

FIG. 7 is a flowchart showing a method of controlling a dual-energy X-ray imaging apparatus according to the exemplary embodiment of the present invention.

FIG. 8 is a flowchart showing an operation of setting a second energy in the control method for the dual-energy X-ray imaging apparatus according to the exemplary embodiment of the present invention.

DETAILED DESCRIPTION OF THE INVENTION

Figure 1:
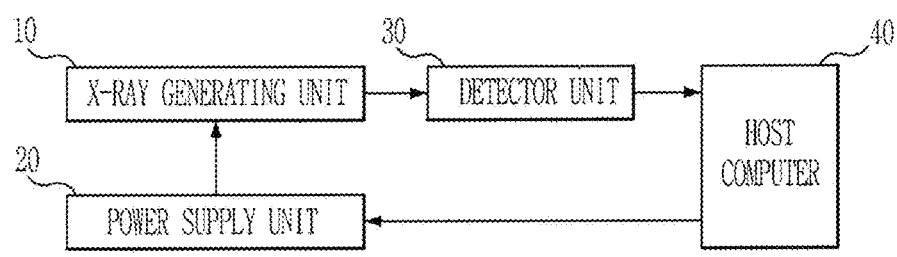
FIG. 1 is a block diagram illustrating a dual-energy X-ray imaging apparatus according to an exemplary embodiment of the present invention.

Hereinafter, preferred embodiments of the present invention will be described with reference to the accompanying drawings, in which like reference numerals refer to like elements throughout. This invention may, however, be embodied in many different forms and should not be construed as limited to the exemplary embodiments set forth herein. In the following description, a detailed explanation of known related functions and constructions may be omitted to avoid unnecessarily obscuring the subject matter of the present invention. Also, terms described herein, which are defined considering the functions of the present invention, may be implemented differently depending on user and operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

In the following description, an X-ray image of a first energy is referred to as an image obtained by radiating an X-ray having the first energy, and an X-ray image of a second energy is referred to as an image obtained by radiating an X-ray having the second energy.

FIG. 1 is a block diagram illustrating a dual-energy X-ray imaging apparatus according to an exemplary embodiment of the present invention.

Referring to FIG. 1, the dual-energy X-ray imaging apparatus according to the exemplary embodiment of the present invention includes an X-ray generating unit 10, a power supply unit 20, a detector unit 30, and a host computer 40. The X-ray generating unit 10 radiates X-rays of a first energy and a second energy to an object, which may be a patient or any other entity being evaluated using the dual-energy X-ray imaging apparatus of the present invention. The power supply unit 20 is configured to provide the X-ray generating unit 10 with operating power. The detector unit 30 detects the X-rays, which have passed through the object, and converts the detected X-rays into corresponding electric signals. The host computer 40 receives the electric signals, which were converted from the X-rays, to obtain the X-ray image of the first energy, and controls the intensity and the quantity of the second energy based on the X-ray image of the first energy.

The host computer 40 operates using predetermined software executing various control procedures to implement the system and method of the present invention. The host computer 40 may include processor such as a central processing unit (CPU), as well as a memory, input and output devices such as the display unit 45 shown in FIGS. 2 and 6, and other components for implementing the various components and features described herein, for example, with reference to FIG. 6.

The X-ray generating unit 10 is configured to generate X-rays by receiving power from the power supply unit 20, with the specific power values determining the energy of each of the generated X-rays. The X-ray generating unit 10 then radiates the X-rays to the object. An X-ray of a first energy and an X-ray of a second energy are sequentially radiated. The intensity and the quantity of each of the first energy and the second energy are determined by the amount of power and the time during which power is supplied by the power supply unit 20.

The first energy may represent a high energy or a low energy. In a case that the first energy represents a high energy, the second energy represents a low energy. In a case that the second energy represents a low energy, the second energy represents a high energy. Both cases are included in exemplary embodiments of the present invention, but the following description will be made in relation that the first energy is a high energy and the second energy is a low energy. For example, high energy X-rays as described herein may have a magnitude of approximately 59 keV, while low energy X-rays as described herein may have a magnitude of approximately 36.2 keV. However, it is understood that such magnitudes are examples only, and X-rays of other energy values may be used for the high and low energy X-rays. Note that high energy and low energy used in the present invention are relative and are set according to the portion to be diagnosed. Regarding the example of the specification, high energy corresponds to 110 kVp, 120 mA, 0.2 seconds and low energy corresponds to 60 kVp, 200 mA, 0.2 seconds.

When the power supply unit 40 provides the X-ray generating unit 10 with a voltage and an electric current, such voltages and electric currents are based on a control signal received from the host computer 50, so the host computer 50 controls the energy of each of the X-rays.

The detector unit 30 detects each of the X-rays that passes through the object. Each X-ray radiated from the X-ray generating unit 10 attenuates while passing through the object, and the X-ray transmission is different at each tissue of the object. Accordingly, the amount of transmission and attenuation of each penetrated X-ray is different at each portion of the object to which the X-ray is radiated.

The tissues showing different X-ray transmission are roughly divided into gas; a soft tissue, such as an adipose tissue, muscles and blood; and a hard tissue containing, for example, a large amount of calcium, such as bones and teeth. Accordingly, the amount of penetrated X-rays varies depending on which tissue is radiated with the X-ray.

In an exemplary embodiment, the detector unit 30 is provided with an image intensifier and a charge coupled device (CCD) camera that are generally known in the art. The detector unit 30 detects an X-ray which has passed through the object, performs image magnification on the detected X-ray through the image intensifier, converts the detected and magnified X-ray into electric signals representing the X-ray image of the detected and magnified X-ray, and transmits the electric signals to the host computer 40.

The host computer 40 obtains the X-ray image by processing the corresponding electric signals from the detector unit 30, and controls each component of the dual-energy X-ray imaging apparatus. In particular, the host computer 40 adjusts the magnitude of power provided to the X-ray generating unit 10 by controlling the power supply unit 20. As a result, the intensity and the amount of the X-rays radiated from the X-ray generating unit 10 are adjusted.

The host computer 40 transmits a signal to the power supply unit 20 such that the power supply unit 20 provides a predetermined high voltage and a predetermined electric current to the X-ray generating unit 10, so that a high energy X-ray is radiated. The voltage and the electric current are set differently at each portion of the object. The radiated high energy X-ray passes through the object, and then proceeds to cause the host computer 40 to generate a corresponding high energy X-ray image in response to the electric signal sent to the host computer 40 via the detector unit 30. The host computer 40 obtains the high energy X-ray image using an X-ray signal corresponding to the high energy X-ray, divides the high energy X-ray image into a bone region, a soft tissue region, and an air region through image segmentation, and sets the intensity and the amount of low energy X-rays to be generated which are suitable for the characteristics of the object based on brightness information of the divided regions.

The host computer 40 transmits, to the X-ray generating unit 10, a signal representing a voltage and an electric current corresponding to the intensity and the amount of the low energy X-rays to be generated, such that the X-ray generating unit 10 radiates a low energy X-ray to the object. The low energy X-ray passing through the object causes the host computer 40 to generate a corresponding low energy X-ray image in response to the electric signal transmitted to the host computer 40 via the detector unit 30. Thereafter, Dual-Energy X-ray Absorptiometry (DEXA), which is also known as DXA, is performed to remove residual images of the bone and the soft tissue, thereby obtaining a clear image desired by a user of the present invention, such as a tester, technician, or diagnostician.

Figure 2:
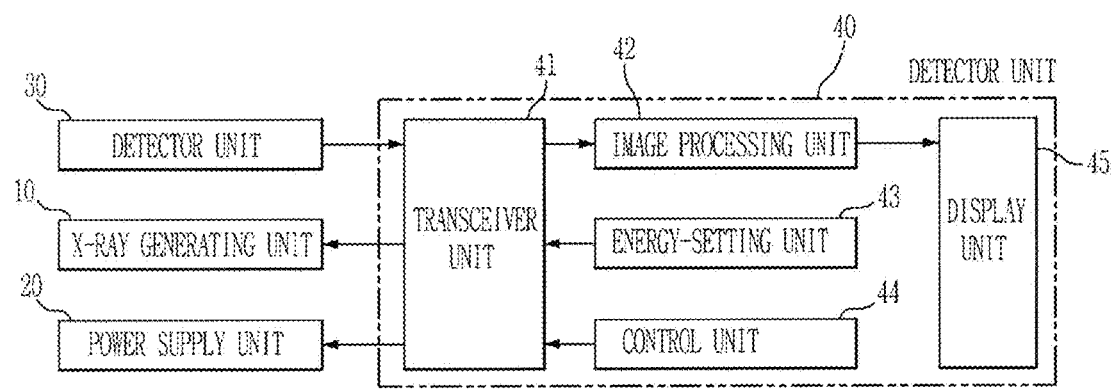
FIG. 2 is a block diagram illustrating a host computer of the dual-energy X-ray imaging apparatus according to the exemplary embodiment of the present invention.

FIG. 2 is a block diagram illustrating the host computer 40 of the dual-energy X-ray imaging apparatus according to the exemplary embodiment of the present invention.

Figure 6:
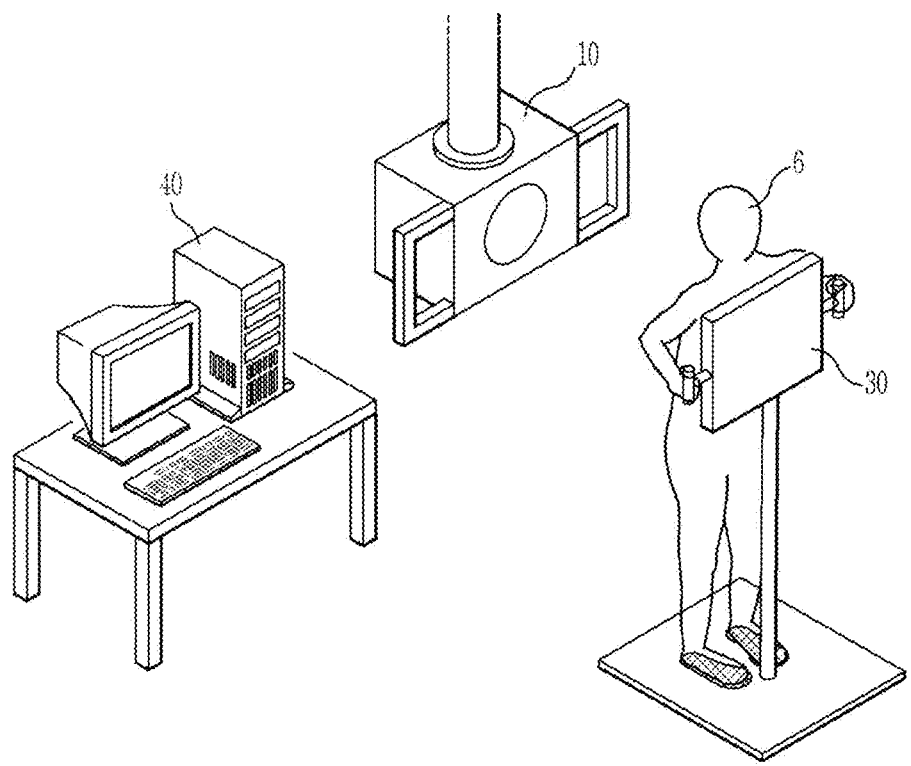
FIG. 6 is a view illustrating the configuration of the dual-energy X-ray imaging apparatus according to the exemplary embodiment of the present invention.

The host computer 40 according to the exemplary embodiment of the present invention includes a transceiver unit 41, an image processing unit 42, an energy-setting unit 43, and a display unit 45. The transceiver unit 41 transmits and receives the electric signals from the detector unit 30 and the power supply unit 20. The image processing unit 42 generates an X-ray image by performing an image processing on the electrical signals representing the X-ray images, which have been transmitted from the detector unit 30. The energy-setting unit 43 sets the intensity and the amount of low energy X-rays to be generated based on the high energy X-ray image. The display unit 45 displays X-ray images through a screen, such as shown in FIG. 6.

The transceiver unit 41 sends, to the power supply unit 20, a control signal representing a voltage and an electric current corresponding to a predetermined high energy to be generated, which may be set in advance, such that an X-ray of the predetermined high energy is radiated. The detector unit 30 detects the high energy X-rays, which have passed through an object, and converts the high energy X-rays into an electric signal. The transceiver unit 41 receives the electric signal and transmits the received electric signal to the energy-setting unit 43 by which the intensity and the amount of the low energy X-rays are set. The transceiver unit 41 sends, to the power supply unit 20, a control signal representing a voltage and an electric current corresponding to the set intensity and the amount of the low energy X-rays to be generated. The detector unit 30 detects the low energy X-rays, which are generated to have the low energy, and which passes through the object, and the detector 30 converts the detected low energy X-rays into an electric signal. The transceiver unit 41 receives the electric signal, and transmits the received electric signal to the image processing unit 42.

In addition, the host computer 40 may further include a control unit 44 configured to control the overall operation of the dual-energy X-ray imaging apparatus. The control unit 44 transmits control signals to the power supply unit 20, the X-ray generating unit 10 and the detector unit 30 through the transceiver unit 41.

Figure 3:
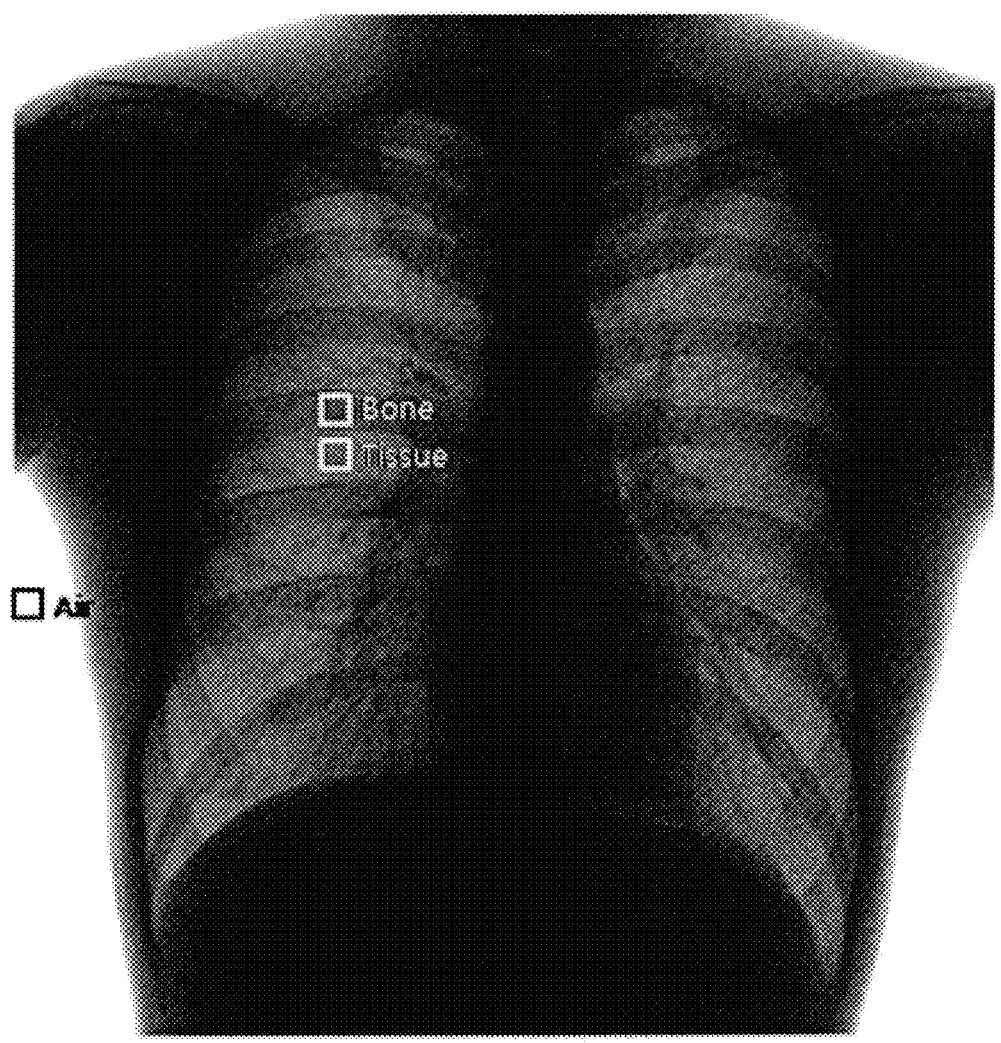
FIG. 3 shows an X-ray image in which a bone, a soft tissue, and air are distinctively represented in respective regions of the X-ray image.

The image processing unit 42 receives an X-ray signal from the transceiver unit 41 to generate an X-ray image. First, the image processing unit 52 receives an X-ray signal corresponding to the high energy X-rays to generate the high energy X-ray image. FIG. 3 shows an example of a chest X-ray image using high energy X-rays. Referring to FIG. 3, the high energy X-ray image has image elements, including groups of pixels, which are distinguished for a bone, soft tissue, and air. Accordingly, the high energy X-ray image may be divided into a bone region, a soft tissue region, and an air region, and the high energy X-ray image is transmitted to the energy-setting unit 43. In general, an X-ray image may be divided through an image segmentation procedure that is generally known in the art.

In addition, if a low energy X-ray signal, corresponding to a low energy X-ray, is transmitted from the detector unit 30 to the image processing unit 42, a corresponding low energy X-ray image is generated. Thereafter, a bone region and a soft tissue region are separated by using the high energy X-ray image and the low energy X-ray image through the DEXA, thereby generating a desired X-ray image. Such image processing through the DEXA will be described later in greater detail.

The energy-setting unit 43 determines the intensity and the amount of low energy X-rays to generate based on brightness information of the divided regions of the high energy X-ray image which has been subjected to image segmentation. First, the energy-setting unit 43 calculates a representative brightness for each divided region of the X-ray image of the high energy, for example, a representative brightness for air ($I_A$), a representative brightness for the soft tissue ($I_S$) and a representative brightness for the bone ($I_B$). Thereafter, the thickness of a portion of the X-ray image corresponding to each divided region is estimated by use of the calculated representative brightness for each divided region and an attenuation coefficient of the portion. The representative brightness represents the average brightness of each divided region. Hereinafter, the average brightness of each divided region will be referred to as a brightness.

Based on the estimated thickness and the calculated brightness, the second energy, that is, the low energy is set such that a difference in attenuation coefficients between the bone and the soft tissue is maximized, and so X-rays with low energy will be used, such that the energy absorption of X-rays by the human body is minimized, resulting in a greater overall health of the patient. A detailed description of such low energy determinations will be made later through equations described herein.

Thereafter, a signal, representing a voltage and an electric current corresponding to the intensity and the amount of the X-rays at a set or determined low energy, is transmitted to the power supply unit 20 through the transceiver unit 41 to generate the corresponding low energy X-ray, such that a clear X-ray image suitable for determining the characteristics and health of the object is obtained.

Hereinafter, the energy-setting process in the energy-setting unit 43 and the image processing in the image processing unit 42 will be described in detail.

As described above, the transmission rate and the attenuation rate of an X-ray are different for each substance to which the X-ray is transmitted. An X-ray image is an image representing the internal structure of an object by use of such a difference in the transmission rate and the attenuation rate. An attenuation coefficient is a quantity measuring the attenuation rate of an X-ray. The attenuation coefficient represents the relationship between the intensity ($I_O$) of an X-ray introduced to an object and the intensity (I) of the penetrated X-ray having passed through thickness (t) of the object. The attenuation coefficient is expressed through Equation 1 shown below:

$$I = I_O * \exp(-\mu t). \tag{1}$$

Herein, $\mu$ represents the attenuation coefficient. The larger that the attenuation coefficient is, the smaller the intensity of the penetrated X-ray is. Accordingly, a larger attenuation coefficient represents a smaller transmission rate of the penetrated X-ray. A smaller attenuation coefficient represents a larger transmission rate of penetrated X-ray.

Figure 4:
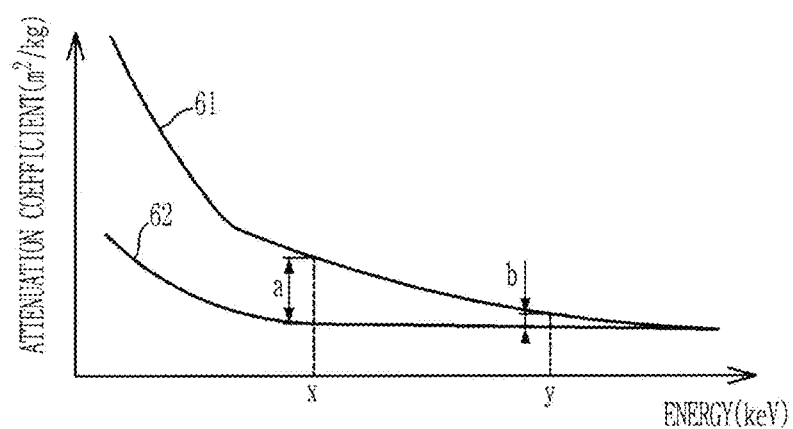
FIG. 4 is a graph showing attenuation coefficients of a bone and a soft tissue.

FIG. 4 is a graph showing example attenuation coefficients of bone and a soft tissue. Referring to FIG. 4, an X-ray having a larger energy shows a smaller attenuation. That is, an X-ray having a high energy penetrates an object better than does an X-ray having a low energy. In addition, the curve representing the attenuation coefficient of the bone is shown above the curve representing the attenuation coefficient of the soft tissue, indicating that the transmission rate of X-rays for the soft tissue is larger than the transmission rate of X-rays for the bone.

Referring to FIG. 4, the difference in attenuation coefficients between the bone and the soft tissue varies with the intensity of the energy. The difference in attenuation coefficients at the X-ray energy of x keV is larger than the difference at the X-ray energy of y keV. That is, the X-ray of a higher energy of y keV produces a smaller difference in attenuation coefficients between the bone and the soft tissue.

As described above, the energy-setting unit 43 measures the thickness of each divided region in the X-ray image of FIG. 3 by use of the brightness and the attenuation coefficient of each divided region. The measuring of the brightness and the thickness of soft tissue, having index T, and of bone, having index B, are expressed through Equations 2 and 3, respectively, as shown below:

$$I_T e^{-\mu_B(\overline{E_1})T_B} = I_B, \quad I_A e^{-\mu_T(\overline{E_1})T_T} = I_T \quad (2)$$

$$T_B = -\frac{\ln I_B - \ln I_T}{\mu_B(\overline{E_1})}, \quad T_T = -\frac{\ln I_T - \ln I_A}{\mu_T(\overline{E_1})}. \quad (3)$$

Herein, $\mu_B(\overline{E_1})$ represents the attenuation coefficient of an X-ray of the first energy for the bone, and $\mu_T(\overline{E_1})$ represents the attenuation coefficient of X-ray of the first energy for the soft tissue, $T_B$ represents the thickness of the bone, and $T_T$ represents the thickness of the soft tissue. $\overline{E_1}$ represents the average energy of a spectrum associated with X-rays having the first energy, and $\overline{E_2}$ represents the average energy of a spectrum associated with X-rays of the second energy.

In order to match the brightness between the first X-ray image obtained from X-rays of the first energy and the second X-ray image obtained from X-rays of the second energy, the second energy is set such that the brightness of the soft tissue of the first X-ray image of the first energy is identical to the brightness of the soft tissue of the second X-ray image of the second energy. The matching of brightness is expressed through Equation 4 shown below, which is obtained by substituting the formula for the soft tissues in Equation 2:

$$w I_T(\overline{E_2}) = I_T(\overline{E_1}) \rightarrow w I_A e^{-\mu_T(\overline{E_2})T_T} = I_T(\overline{E_1}) \quad (4)$$

Herein, w represents a weight associated with an output of the power supply unit 20 used to match the brightness information in consideration of the difference between the first energy and the second energy. For example, in a case that an X-ray of a first energy is generated with an output of 100 mAs, and if w is 1.5, an X-ray of a second energy is generated with an output of 150 mAs. Such electrical current values may be used to represent the energy values of the X-rays if, for example, an X-ray generating unit 10 operates at a specific peak voltage, such as, for example, a tube voltage of 110 peak kilovolts (kVp). Alternatively, other parameters which characterize the X-ray energies generated and output by the X-ray generating unit 10 may be used in Equations 2-4.

A second energy is determined to satisfy a first condition, in which the difference $|\mu_B(\overline{E_2}) - \mu_T(\overline{E_2})|$ in the attenuation coefficients between the bone and the soft tissue is maximized, as well as to satisfy a second condition in which the energy absorption of the soft tissue is minimized, and also to satisfy Equation 4 at the second energy. The determined second energy represents a second energy optimized for obtaining the second energy X-ray image of the object. If the second energy is determined or set, w may be calculated using a predetermined X-ray spectrum library stored in a memory of the host computer 40. That is, the second energy is determined based on Equation 4 and the first and second conditions described herein.

As described above, if the energy-setting unit 43 sets the intensity and the amount of the second energy, the energy-setting unit 43 generates a control signal to the power supply unit 20, and the power supply unit 20 outputs a voltage and an electric current corresponding to the set intensity and the amount of the second energy to generate an X-ray of the second energy. The detector unit 30 detects the X-ray of the second energy, which has passed through an object, and generates a corresponding electric signal which is transmitted to the host computer 40. The image processing unit 40 of the host computer 40 generates an X-ray image of the second energy from the electric signal.

According to the exemplary embodiment of the present invention, the image processing performed on the X-ray image is implemented by the DEXA, and the first energy and the second energy represent a high energy and a low energy, respectively. According to DEXA, the natural logarithms are determined for the intensities or brightness of a first energy image based on a first energy and a second energy image based on a second energy, and then the difference in such logarithmic values between the first and second images is obtained in consideration of a weight, thereby extracting an image from the original X-ray image and having a desired portion more clearly distinguishing between the bone and the soft tissue.

The use of DEXA in conjunction with the exemplary embodiment of the present invention is as follows: differences in image intensities for the soft tissue and for bone are determined according to Equations 5 and 6, where the variables I with indicative subscripts represent the natural logarithm of the image intensities or brightness, with $$I_{bone} = I_H - w_b I_L \quad (5)$$

$$I_{soft} = I_H - w_s I_L \quad (6)$$

Alternatively, the equation (5) may be: $I_{bone} = I_L w_b - I_H$.

$I_L$ and $I_H$ represent the logarithm of the intensity of a low energy image and a high energy image, respectively, $I_{soft}$ and $I_{bone}$ represent the logarithm of the intensity of portions of the soft tissue and of the bone in the X-ray images being processed, respectively, and $w_s$ and $w_b$ represent weights of the soft tissue and of the bone, respectively, which are expressed through Equations 7-8, respectively, below:

$$w_b = \frac{\mu_{bone}(E_H)}{\mu_{bone}(E_L)} \quad (7)$$

$$w_s = \frac{\mu_{soft}(E_H)}{\mu_{soft}(E_L)}. \quad (8)$$

Herein, $\mu_{bone}(E_H)_{represents}$ the attenuation coefficient of a high energy X-ray for a bone, and $\mu_{bone}(E_L)_{represents}$ the attenuation coefficient of a low energy X-ray for a bone. $\mu_{soft}(E_H)$ represents the attenuation coefficient of a high energy X-ray for the soft tissue, and $\mu_{soft}(E_L)$ represents the attenuation coefficient of a low energy X-ray for the soft tissue.

The weights $w_s$ and $w_b$ are obtained through Equations 7 and 8, and weights $W_s$ and $W_b$ are then substituted in Equations 5 and 6 to separate the image regions of either a bone and/or a soft tissue from the high energy X-ray image, thereby to obtain a desired clear image.

In this case, if the low energy is not determined as a predetermined statistical value and but is determined based on the first and second conditions and Equation 4 as described herein, the characteristics of the object are reflected by and shown in the X-ray images, thereby obtaining a desired image in which a bone is more clearly distinguished from a soft tissue. In addition, the use and the absorption of X-rays in the soft tissue is minimized, and thus the exposure dose of X-rays to a patient during the X-ray photography is reduced.

Although the dual-energy X-ray imaging technology according to the exemplary embodiment of the present invention uses DEXA, the present invention is not limited thereto.

Figure 5A:
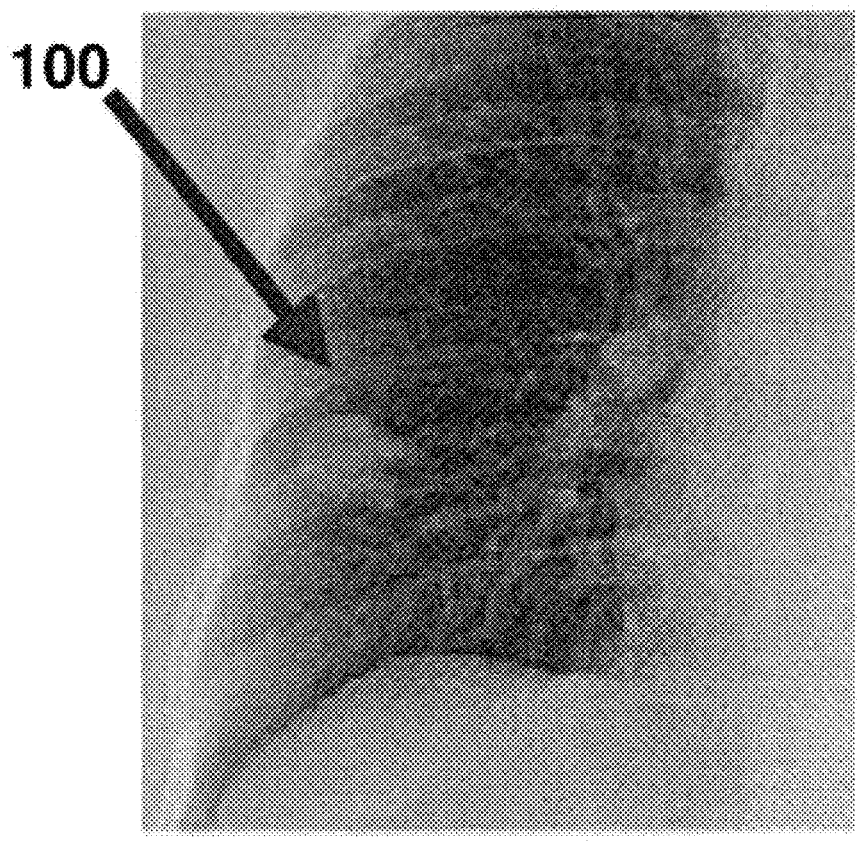
FIG. 5A shows an X-ray image from conventional chest X-ray photography in the prior art.
Figure 5B:
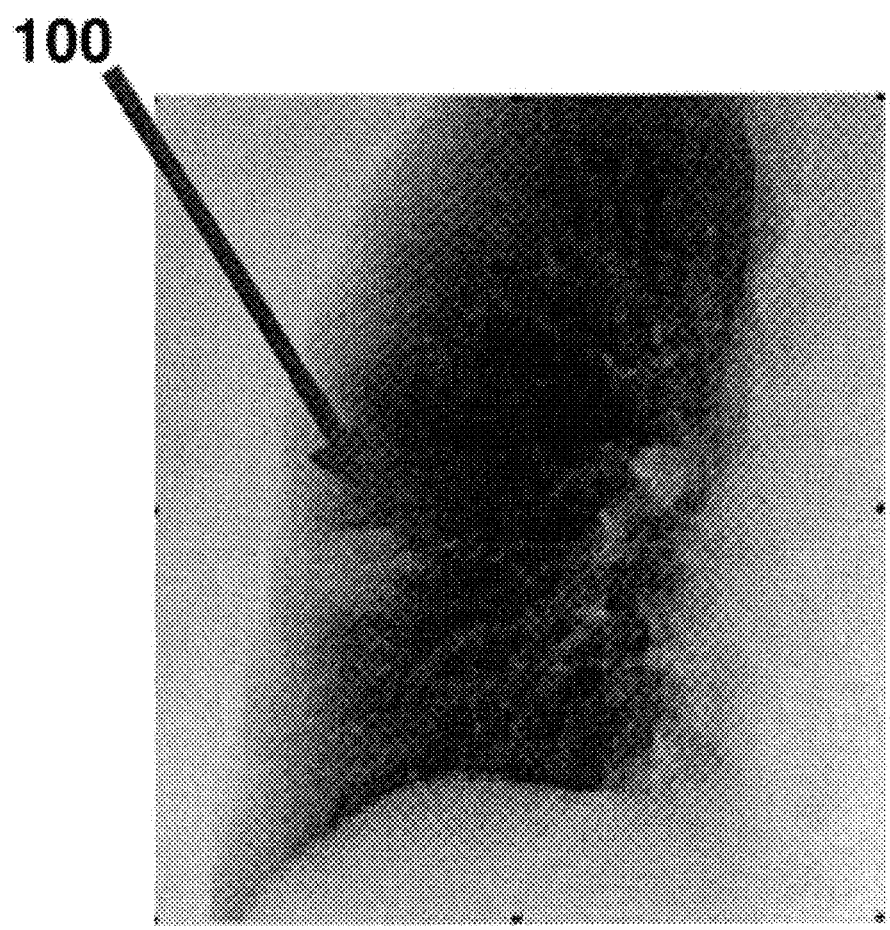
FIG. 5B shows an X-ray image in which a bone tissue is omitted according to the dual-energy X-ray imaging apparatus of the exemplary embodiment of the present invention.
Figure 5C:
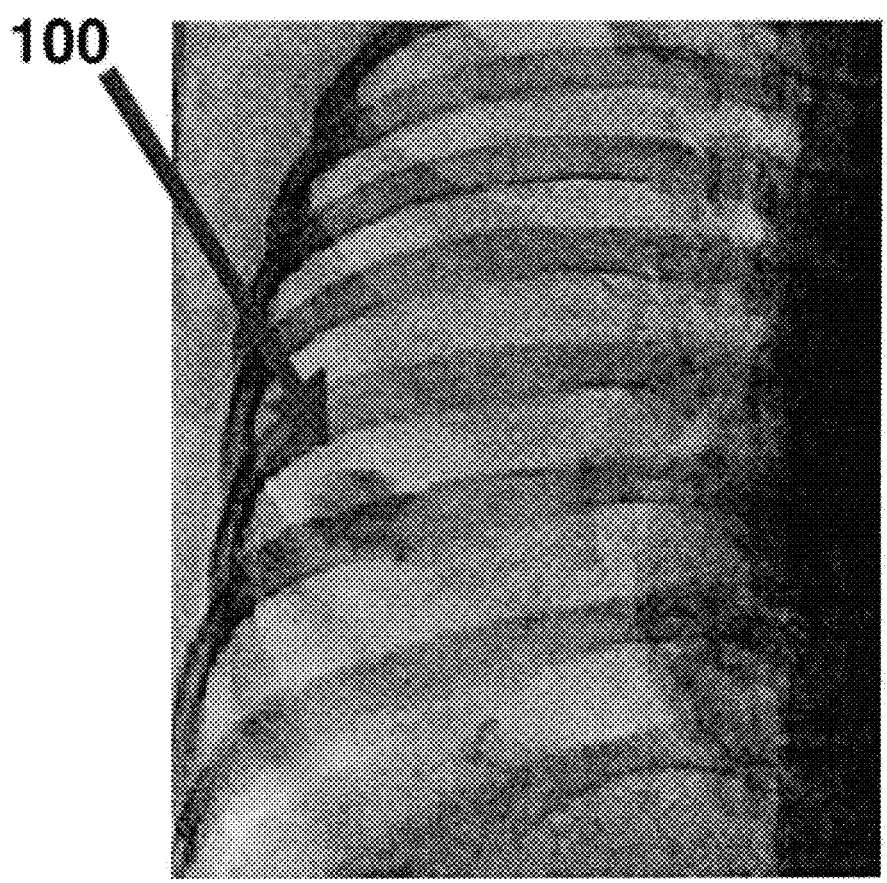
FIG. 5C shows an X-ray image in which a soft tissue is omitted according to the dual-energy X-ray imaging apparatus of the exemplary embodiment of the present invention.

Referring to FIGS. 5A-5C, FIG. 5A shows an X-ray image of a conventional chest X-ray photography in the prior art. FIG. 5B shows an X-ray image in which a bone tissue is omitted according to the dual-energy X-ray imaging apparatus of the exemplary embodiment of the present invention. FIG. 5C shows an X-ray image in which a soft tissue is omitted according to the dual-energy X-ray imaging apparatus of the exemplary embodiment of the present invention.

Referring to FIG. 5A, it is believed that lesions are shown inside the right side of the example X-ray image, and are suspected of being a solitary pulmonary nodule (SPN) 100. By removing the bone tissue through the dual-energy X-ray photography of the present invention, the X-ray image shown in FIG. 5B is obtained. By examining the X-ray image of FIG. 5B, a diagnosis for the presence of the SPN 100 is readily and more clearly made. If the soft tissue is removed through the dual-energy X-ray photography of the present invention, the X-ray image of FIG. 5C is obtained. In FIG. 5C, the portion of the X-ray image suspected of being the lesion has a shade similar to the rib, so the nodule 100 is believed to contain lime.

FIG. 6 is a view illustrating the configuration of the dual-energy X-ray imaging apparatus according to the exemplary embodiment of the present invention.

Referring to FIG. 6 in conjunction with FIGS. 1-2, the X-ray generating unit 10 is installed to face the detector unit 30 that is spaced apart from the X-ray generating unit 10 by a predetermined distance, and the power supply unit 20 is connected to the X-ray generating unit 10 to supply the voltage and the electric current such that X-rays are generated by the X-ray generating unit 10 to pass through an object 6, such as a patient adjacent to the detector unit 30, and with such transmitted X-rays detected by the detector unit 30.

According to the control procedures operated by the host computer 40, the power supply unit 20 provides a high voltage and an electric current that are set in advance.

If a human serves as the object 6 shown, for example, in FIG. 6, the object 6 takes different poses or postures according to each portion of the body to be X-ray photographed in front of the detector unit 30. For chest X-ray photography, the object 6 stands and is oriented in order to closely push his/her chest onto or substantially adjacent to the detector unit 30 while orienting his/her back to the X-ray generating unit 10. The detector unit 30 detects any X-ray which is radiated from the X-ray generating unit 10 and passes through the object 6, converts the detected X-ray to an electric signal, and transmits the electric signal to the host computer 40, which is connected to the detector unit 30 shown in FIGS. 1-2.

The host computer 40 is connected to the detector unit 30 and the power supply unit 20 to transmit a signal representing a voltage and an electric current, and to obtain a high energy X-ray image based on the transmitted electric signal from the detector unit 30 generated to correspond to the X-ray.

The energy-setting unit 43 of the host computer 40 divides the obtained high energy X-ray image into a bone region, a soft tissue region and an air region through image segmentation, as shown in FIG. 3, and sets the optimized intensity and the amount of a low energy X-ray to generate and transmit from the X-ray generating unit 10 using the brightness of each divided region. In addition, the energy-setting unit 43 sends, to the power supply unit 20, a signal representing the voltage and the electric current corresponding to the established intensity and the amount of the low energy X-ray.

If the power supply unit 20 radiates the low energy X-ray to the object 6, an electric signal corresponding to the low energy X-ray is transmitted to the transceiver unit 41 of the host computer 40, and the image processing unit 42 removes residual images of the bone and the soft tissue from the high energy and low energy X-ray images using the difference in attenuation coefficients at each X-ray energy. The result of the residual removal is output through the display unit 45, so that a test administrator determines whether the object 6 has a disease.

The configuration of the dual-energy X-ray imaging apparatus shown in FIG. 6 is provided as one exemplary embodiment, and the present invention is not limited thereto. For example, the object may be subject to the X-ray photography in a lying or sitting position. In addition, the position of each component forming the dual-energy X-ray imaging apparatus is not limited to FIG. 6.

Hereinafter, a method of controlling a dual-energy X-ray imaging apparatus according to an exemplary embodiment of the present invention will be described. In the following description, in an exemplary embodiment, the first energy and the second energy represent the high energy and the low energy, respectively.

FIG. 7 is a flowchart showing a method of controlling the dual-energy X-ray imaging apparatus according to the exemplary embodiment of the present invention.

Referring to FIG. 7, an X-ray of a high energy, the magnitude of which is set in advance, is generated and radiated to an object 6 in step 81. The value of the high energy is set to vary according to a diagnosis portion. In general, for the chest X-ray photography, the high energy is generated by use of a tube voltage of 110 peak kilovolts (kVp) and a tube current of 120 mA. The radiated high energy X-ray passes through the object 6, and a corresponding electric signal is transmitted to the host computer 40 from the detector unit 30.

By performing image processing on the electric signal corresponding to the high energy X-ray, a high energy X-ray image of the high energy X-ray is obtained. Then, the obtained high energy X-ray image is divided into a bone region, a soft tissue region, and an air region in step 82, and the intensity and the amount of low energy X-rays are set to be optimized for X-ray photography of the object 6 based on brightness information of each divided region of the high energy X-ray image in step 83.

A signal representing the voltage and current signal, corresponding to the set intensity and the amount of the low energy X-ray, is transmitted such that the low energy X-ray is radiated to the object 6 in step 84. The radiated low energy X-ray passes through the object 6, and is converted to an electric signal by the detector unit 30, which is then transmitted to the host computer 40.

The low energy X-ray signal is used to generate the low energy X-ray image through image processing in step 85. Using the difference in attenuation coefficients of X-rays between the bone and the soft tissue, the X-ray absorption effect for the bone or the X-ray absorption effect for the soft tissue is selectively removed from the high energy X-ray image and from the low energy X-ray image to obtain a dual-energy X-ray image in step 86. The process of removing the X-ray absorption effect for the bone and the soft tissue is implemented through the generally known DEXA method, and has been described above in connection with Equations 1 to 8 in one exemplary embodiment. However, the process of removing the X-ray absorption effect according to the present invention is not limited thereto.

FIG. 8 is a flowchart showing an operation of setting the second energy in the control method for the dual-energy X-ray imaging apparatus according to the exemplary embodiment of the present invention.

Referring to FIG. 8, first, a brightness for each divided region of the X-ray image of the high energy is calculated in step 91. For example, a representative brightness for air ($I_A$), a representative brightness for the soft tissue ($I_S$), and a representative brightness for the bone ($I_B$) are calculated. The calculating of brightness is generally known in the art, and the description thereof will be omitted.

Thereafter, the thickness of each of the bone and the soft tissue is estimated by use of the calculated brightness for each region and an attenuation coefficient of each of the bone and the soft tissue in step 92. The representative brightness represents the average brightness of each divided region. The estimating of the thickness of the bone and the soft tissue is achieved using Equations 2 and 3 described herein.

$$I_T e^{-\mu_B(\overline{E_1})T_B} = I_B, \; I_A e^{-\mu_T(\overline{E_1})T_T} = I_T \quad (2)$$

$$T_B = -\frac{\ln I_B - \ln I_T}{\mu_B(\overline{E_1})}, \; T_T = -\frac{\ln I_T - \ln I_A}{\mu_T(\overline{E_1})}. \quad (3)$$

Herein, $\mu_B(\overline{E_1})$ represents the attenuation coefficient of an X-ray of the first energy for the bone, and $\mu_T(\overline{E_1})$ represents the attenuation coefficient of X-ray of the first energy for the soft tissue, $T_B$ represents the thickness of the bone, and $T_T$ represents the thickness of the soft tissue. $\overline{E_1}$ represents the average energy of a spectrum associated with X-rays having the first energy, and $\overline{E_2}$ represents the average energy of a spectrum associated with X-rays having the second energy.

The intensity and the amount of the low energy X-rays, that is, X-rays having the second energy, are set based on the calculated brightness and the estimated thickness in step 93. In particular, the second energy is determined to satisfy the first condition in which the difference $|\mu_B(\overline{E_2})-\mu_T(\overline{E_2})|$ in the attenuation coefficient between the bone and the soft tissue is maximized, to satisfy the second condition that the energy absorption of the soft tissue is minimized, and to satisfy that the brightness at the second energy is matched according to Equation 4 below.

$$wI_T(\overline{E_2}) = I_T(\overline{E_1}) \rightarrow wI_A e^{-\mu_T(\overline{E_2})T_T} - I_T(\overline{E_1}),$$

$$|\mu_B(\overline{E_2}) - \mu_T(\overline{E_2})| \quad (4)$$

Equation 4 represents a condition used to match the brightness between the X-ray images of the two energies, and w represents a weight based on the difference in energy. In addition, the first condition is required to distinguish the bone from the soft tissue, and the second condition is required to minimize the X-ray exposure dose to the object 6, such as a patient.

Hereinafter, a process of performing the chest X-ray photography on the object according to an exemplary embodiment of the present invention will be described. In the following description, the first energy and the second energy represent the high energy and the low energy, respectively.

First, an X-ray of a high energy is radiated to the chest of the object 6. To this end, a tube voltage of, for example, 120 kVp is delivered from the power supply unit 20 to the X-ray generating unit 10. The high energy X-ray, having passed through the chest of the object 6, is converted to an electric signal by the detector unit 30, and is transmitted to the host computer 40.

The image processing unit 42 of the host computer 40 obtains a high energy X-ray image corresponding to the high energy X-ray converted in the form of an electric signal, and divides the high energy X-ray image into a bone region, a soft tissue region, and an air region through image segmentation. The result of X-ray image segmentation is transmitted to the energy-setting unit 43.

The energy-setting unit 43 sets a low energy that minimizes the energy absorption of the object 6, and maximizes the difference in attenuation coefficients between the bone and the soft tissue based on brightness information for each divided region of the X-ray image of the high energy. The minimizing of the energy absorption is performed to minimize the X-ray exposure doses to the human body, such as a patient as the object 6. The detailed description of setting the low energy has been made above with reference to FIG. 8.

The transceiver unit 41 of the host computer 40 sends the power supply unit 20 a signal representing the voltage and the electric current corresponding to the set low energy for the low energy X-ray, such that the X-ray generating unit 10 generates and radiates the low energy X-ray to the object 6. According to this exemplary embodiment, a tube voltage of, for example, 60 kVp is provided in response to the intensity and the amount of the low energy determined above.

The low energy X-ray, having passed through the object 6, is converted to an electric signal by the detector unit 30, and then is transmitted to the host computer 40.

Figure 9A:
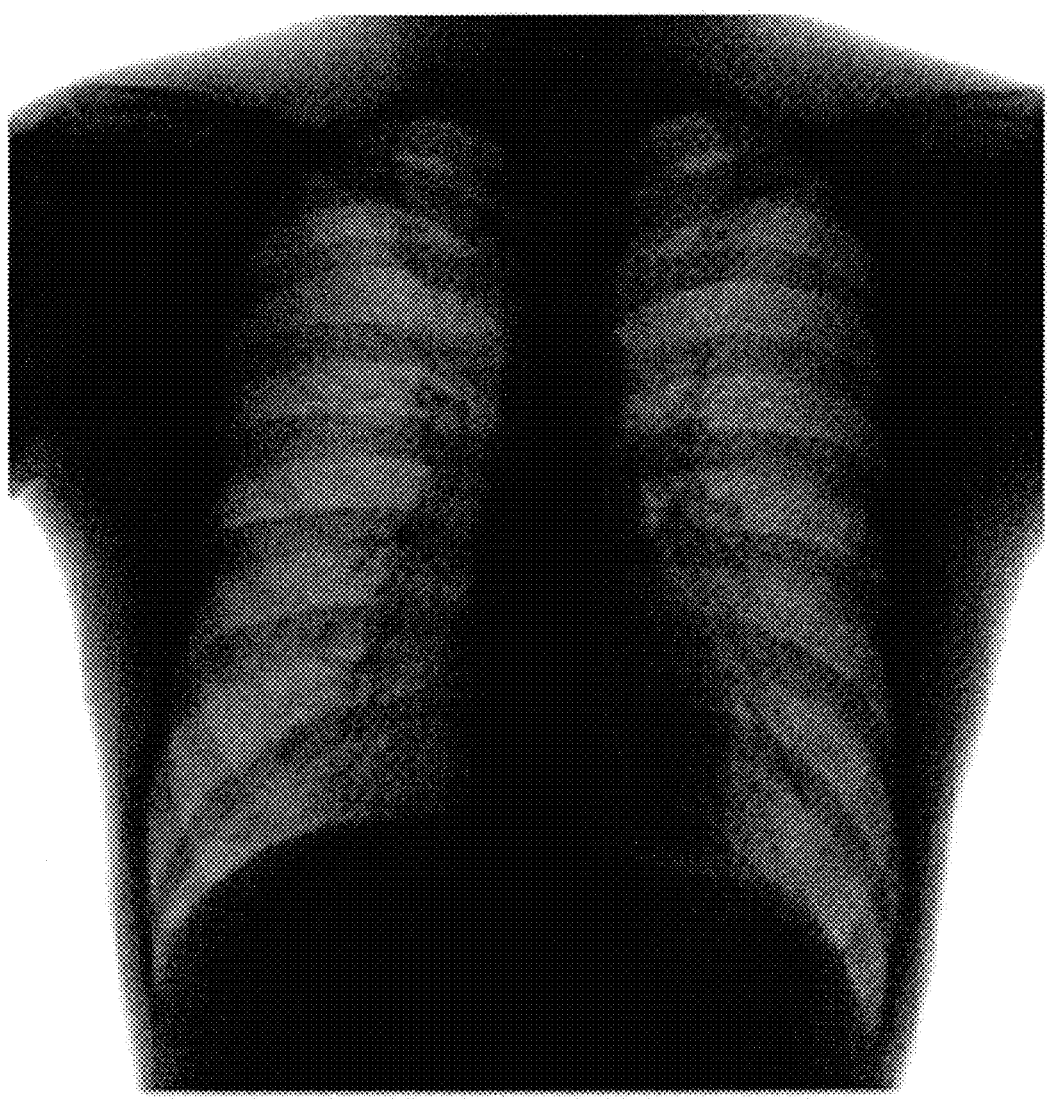
FIG. 9A shows a chest X-ray image obtained with a high energy X-ray using the dual-energy X-ray imaging apparatus according to the exemplary embodiment of the present invention.
Figure 9B:
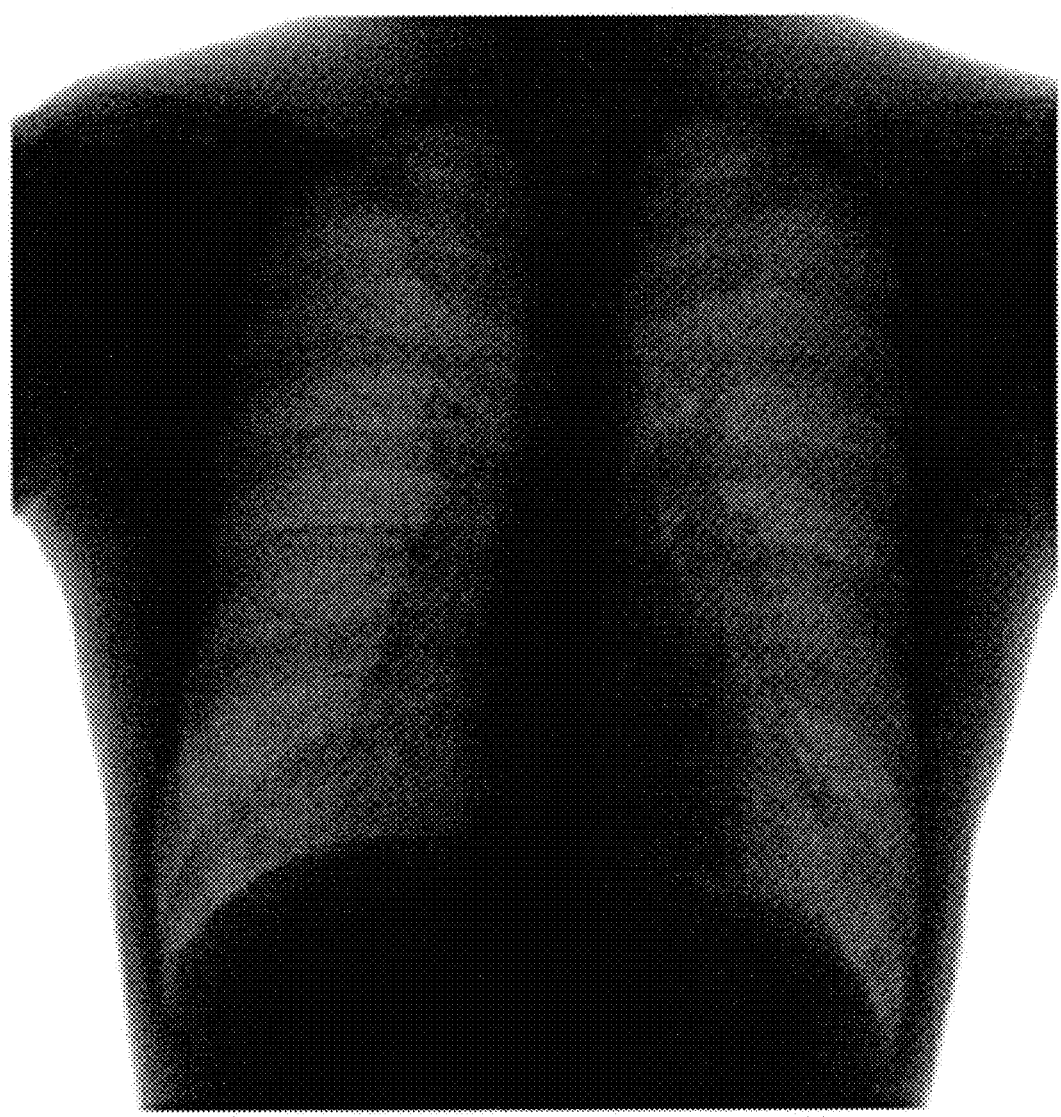
FIG. 9B shows a chest X-ray image obtained with a low energy X-ray using the dual-energy X-ray imaging apparatus according to the exemplary embodiment of the present invention.

The host computer 40 obtains a low energy X-ray image from the transmitted electric signal. FIGS. 9A-9B show chest X-ray images according to the exemplary embodiment of the present invention, in which FIG. 9A shows a chest X-ray image of a high energy X-ray obtained by the dual-energy X-ray imaging apparatus according to the exemplary embodiment of the present invention, and FIG. 9B shows a chest X-ray image of a low energy X-ray obtained by the dual-energy X-ray imaging apparatus according to the exemplary embodiment of the present invention.

Figure 10:
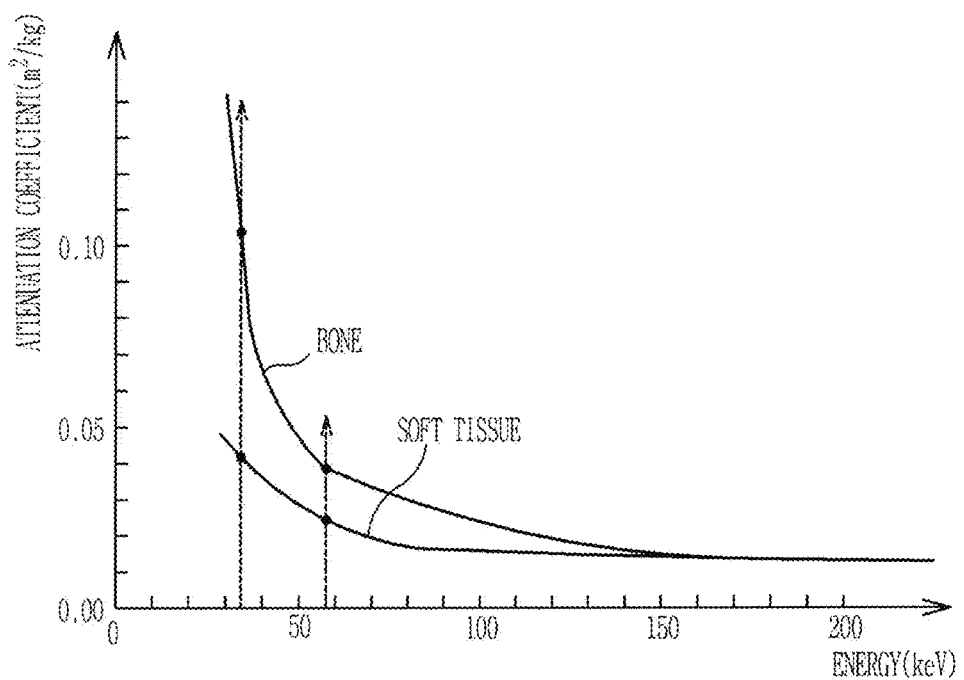
FIG. 10 is a graph showing attenuation coefficients of bone and soft tissue according to X-ray energy used in the control method for the dual-energy X-ray imaging apparatus of the exemplary embodiment of the present invention.

The host computer 40 obtains the dual-energy X-ray image for a bone or a soft tissue based on the attenuation coefficient of a high energy X-ray for each of the bone and the soft tissue, and the attenuation coefficient of a low energy X-ray for each of the bone and the soft tissue. FIG. 10 is a graph showing attenuation coefficients of bone and soft tissue according to the X-ray energy using the control method for the dual-energy X-ray imaging apparatus of the exemplary embodiment of the present invention.

Referring to FIG. 10, the average energy of an energy spectrum generated at 60 kVp is 36.2 keV, and the attenuation coefficients of the bone and the soft tissue corresponding to the energy of 36.2 keV are found from the graph to be approximately 0.105 m²/kg and 0.04 m²/kg, respectively. As the average energy of energy spectrum generated at 120 kVp is 59 keV, and the attenuation coefficients of the bone and the soft tissue corresponding to the energy of 59 keV are found in the graph to be approximately 0.105 m²/kg and 0.04 m²/kg, respectively. If the found attenuation coefficients of the bone and the soft tissue at different energy levels are substituted into Equations 5 to 8, an X-ray image is obtained by the present invention which does not represent an absorption effect due to the bone and such an obtained X-ray image does not represent an absorption effect due to the soft tissue.

Figure 11A:
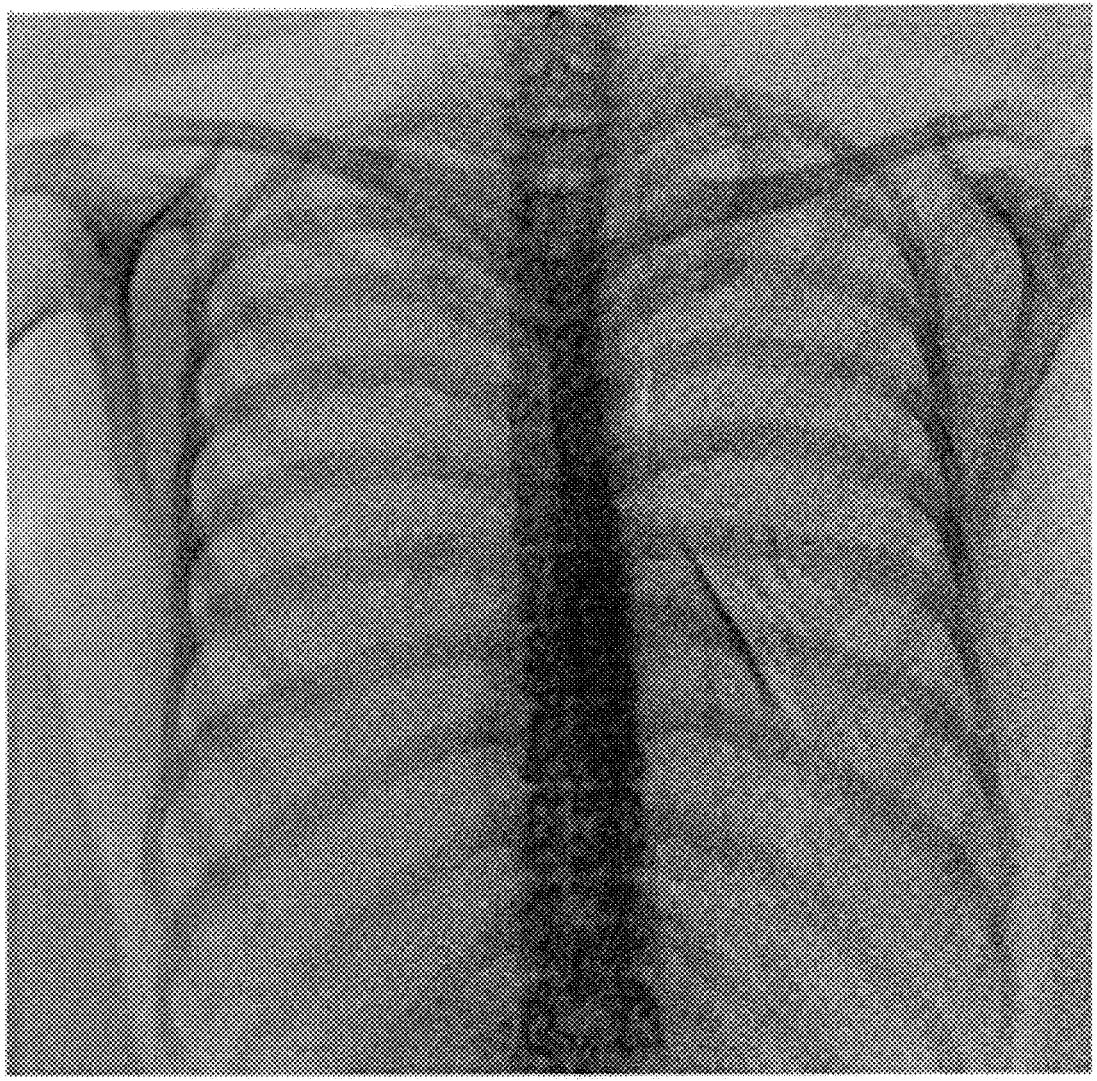
FIGS. 11A-11B show resulting images obtained by the control method for the dual-energy X-ray imaging apparatus according to the exemplary embodiment of the present invention.
Figure 11B:
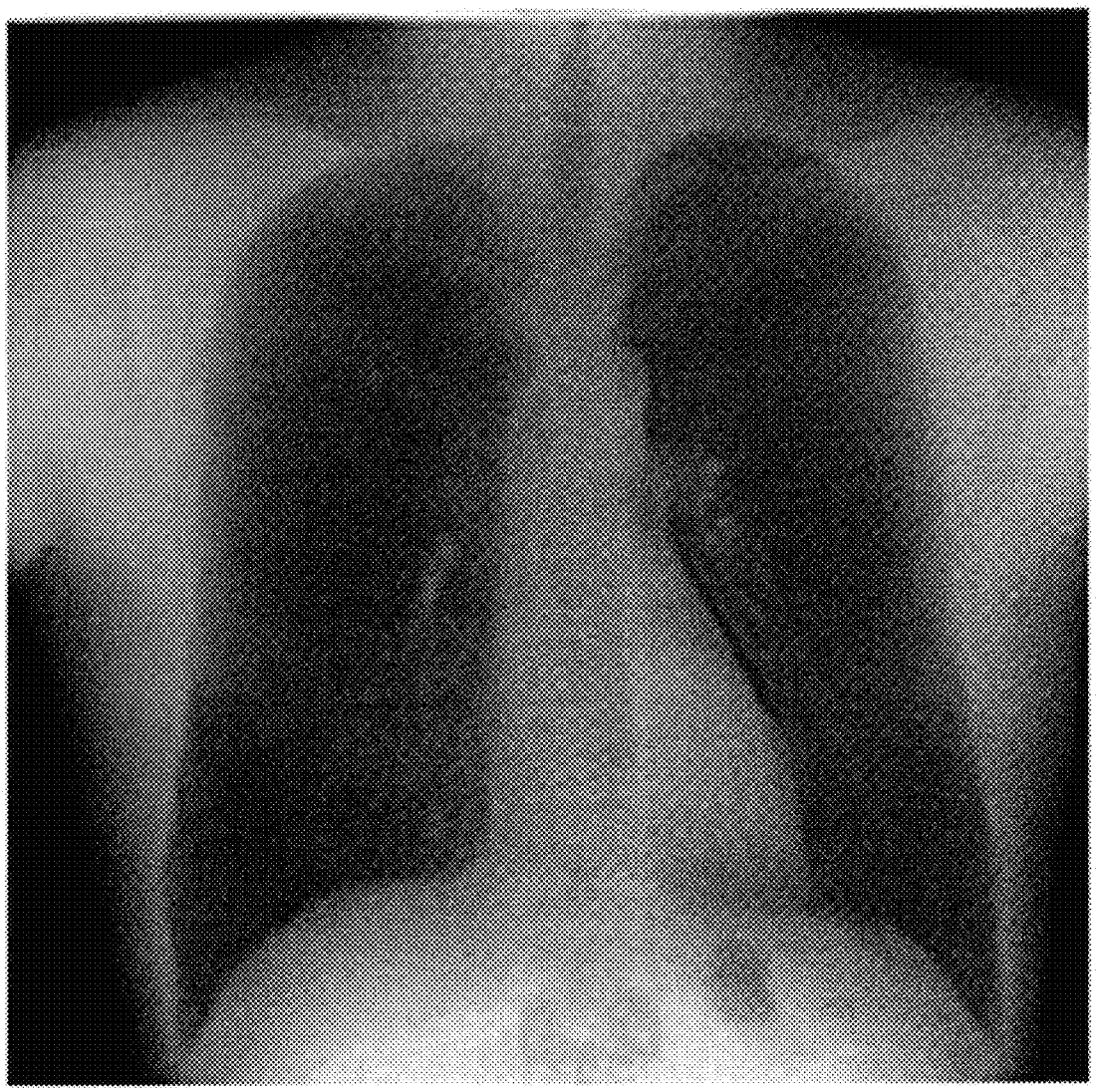

FIGS. 11A and 11B are results of X-ray images obtained by the control method for the dual-energy X-ray imaging apparatus according to the exemplary embodiment of the present invention. FIG. 11A represents a rib X-ray image that is obtained by removing the X-ray absorption effect due to soft tissue from a single-energy X-ray image shown in FIG. 9A, and FIG. 11B is a soft tissue X-ray image that is obtained by removing the X-ray absorption effect due to bone from a single-energy X-ray image shown in FIG. 9A. FIGS. 11A-11 are obtained by the present invention by processing, in the host computer 40, the high energy X-ray image in FIG. 9A using the low energy X-ray image of FIG. 9B to remove the soft tissue image regions, resulting in FIG. 11A, and to remove the bone tissue image regions, resulting in FIG. 11B. In this manner, the test administrator obtains a desired X-ray image optimized for a predetermined portion to be photographed with X-rays. In addition, since the low energy X-ray image is obtained by adjusting the X-ray energy to correspond to the characteristics of the object, the resulting X-ray image is clear and the X-ray exposure doses to the object, such as a patient, are reduced, and thus the safety in using X-ray photography is ensued.

The above-described apparatus and methods according to the present invention can be implemented in hardware, firmware or as software or computer code that can be stored in a recording medium such as a CD ROM, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered in such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

Although a few exemplary embodiments of the present invention have been shown and described, it will be appreciated by those skilled in the art that various changes in form and details may be made in these exemplary embodiments without departing from the principles and the spirit and scope of the present invention, as defined in the appended claims and their equivalents.

What is claimed is:

1. A dual-energy X-ray imaging apparatus comprising:
   an X-ray generating unit configured to sequentially radiate a first energy X-ray having a first energy and a second energy X-ray having a second energy;
   a power supply unit configured to supply power to the X-ray generating unit;
   a detector unit configured to detect the first and second energy X-rays, which are radiated from the X-ray generating unit, and to convert the detected first and second energy X-rays into corresponding electric signals;
   a host computer configured to receive the electric signals such that a first energy X-ray image using the first energy X-ray is obtained, and to set the second energy using a brightness of the first energy X-ray image for obtaining a second energy X-ray image using the second energy X-ray; and
   an energy-setting unit configured to set an amount of the second energy x-rays such that a brightness of a soft tissue region of the first energy X-ray image is identical to a brightness of a soft tissue region of the second energy X-ray.

2. The dual-energy X-ray imaging apparatus of claim 1, further comprising an image processing unit configured to obtain the first energy X-ray image and to divide the first energy X-ray image into a bone region, a soft tissue region, and an air region for each of a bone, a soft tissue, and air, respectively, using an image segmentation method.

3. The dual-energy X-ray imaging apparatus of claim 2, wherein the energy-setting unit sets the amount of the second energy x-rays using a respective brightness of each of the divided regions.

4. The dual-energy X-ray imaging apparatus of claim 1, wherein the energy setting unit sets the second energy, which maximizes a difference in attenuation coefficients between a bone and the soft tissue and minimizes energy absorption of the soft tissue.

5. The dual-energy X-ray imaging apparatus of claim 1, wherein the energy-setting unit sets the second energy, which maximizes a difference in an attenuation coefficient between a bone and the soft tissue, minimizes energy absorption of the soft tissue, and satisfies:

$$wI_T(\overline{E_2})=I_T(\overline{E_2}) \rightarrow wI_A e^{-\mu T(\overline{E_2})T_T}=I_T(\overline{E_1}),$$

wherein w represents a weight of an output of the power supply unit, $I_T(\overline{E_1})$ represents the brightness of the soft tissue region of the first energy X-ray image, $I_T(\overline{E_2})$ represents the brightness of the soft tissue region of the second energy X-ray image, $\overline{E_1}$ represents an average energy of a spectrum of the first energy X-ray, and $\overline{E_2}$ represents an average energy of a spectrum the second energy X-ray, $\mu T$ represents the attenuation coefficient of the soft tissue, $T_T$ represents a thickness of the soft tissue, $(I_A)$ is a representative brightness for Air (I=brightness, A=Air).

6. The dual-energy X-ray imaging apparatus of claim 1, wherein an image processing unit obtains a dual-energy image by obtaining the first X-ray image and the second X-ray image, and by removing at least one of an X-ray absorption effect of a bone and an X-ray absorption effect of the soft tissue from the first energy X-ray image and the second energy X-ray image using a difference in attenuation characteristics of X-rays between the bone and the soft tissue.

7. A method of controlling a dual-energy X-ray imaging apparatus, the method comprising:
   radiating a first energy X-ray having a first predetermined energy;
   converting the first energy X-ray into a first electric signal;
   obtaining a first energy X-ray image using the first electric signal;
   setting a second energy of a second energy X-ray using a brightness of the first energy X-ray image;
   setting the amount of the second energy X-ray such that a brightness of a soft tissue region of the first energy X-ray image is identical to a brightness of a soft tissue region of a second energy X-ray image;
   obtaining the second energy X-ray image by radiating the second energy X-ray having the set second energy; and
   obtaining a dual-energy X-ray image from the first and second energy X-ray images.

8. The method of claim 7, wherein the first predetermined energy is greater in magnitude than the second energy.

9. The method of claim 7, further comprising performing an image segmentation to divide the obtained first energy X-ray image into a bone region, a soft tissue region, and an air region corresponding to a bone, a soft tissue, and air, respectively.

10. The method of claim 9, wherein the setting of the second energy comprises:
    calculating a brightness value of each of the divided regions;
    estimating a thickness value of each of the bone and the soft tissue using each calculated brightness and an attenuation coefficient of each of the bone and the soft tissue; and
    using the calculated brightness value and the estimated thickness value to set the second energy.

11. The method of claim 10, wherein the step of using the calculated brightness values and the estimated thickness values includes determining the second energy to match the brightness of the soft tissue of the first energy X-ray image to the brightness of a soft tissue of the second energy X-ray image, maximizing a difference in an attenuation coefficient between the bone and the soft tissue, and minimizing energy absorption of the soft tissue.

12. The method of claim 10, wherein the step of using the calculated brightness values and the estimated thickness values includes determining the second energy which maximizes a difference in an attenuation coefficient between the bone and the soft tissue, and minimizes energy absorption of the soft tissue at the second energy, and satisfies:

$$wI_T(\overline{E_2}) = I_T(\overline{E_2}) \rightarrow wI_A e^{-\mu T(\overline{E_2})T_T} = I_T(\overline{E_1}),$$

wherein w represents a weight of an output of a power supply unit, $I_T(\overline{E_1})$ represents the brightness of the soft tissue region of the X-ray image of the first energy, $I_T(\overline{E_2})$ represents the brightness of the soft tissue region of the X-ray image of the second energy, $\overline{E_1}$ represents an average energy of a spectrum of the first energy, and $\overline{E_2}$ represents an average energy of a spectrum of the second energy, $\mu T$ represents the attenuation coefficient of the soft tissue, $T_T$ represents a thickness of the soft tissue, $(I_A)$ is a representative brightness for Air (I=brightness, A=Air).

13. The method of claim 7, wherein the obtaining of the dual-energy X-ray image includes removing an X-ray absorption effect of at least one of a bone and a soft tissue from the first energy X-ray image and from the second energy X-ray image using a difference in attenuation characteristics of X-rays between the bone and the soft tissue.

14. A dual-energy X-ray imaging apparatus comprising:
an X-ray generating unit for radiating first and second X-rays;
a detector unit for detecting the first and second X-rays and for generating corresponding first and second electric signals, respectively;
a processor, responsive to the first electric signal, for generating a first image, for processing the first image to determine an energy value of the second X-ray, and for generating a second image from the second electric signal,
wherein the processor sets amount of the second X-ray such that a brightness of a soft tissue region of the first image is identical to a brightness of a soft tissue region of the second image.

15. The dual-energy X-ray imaging apparatus of claim 14, wherein the first X-ray has a first energy value, and the second X-ray has the determined energy value as a second energy value, with the first energy value having a magnitude greater than that of the second energy value.

16. The dual-energy X-ray imaging apparatus of claim 14, wherein the processor processes the first image to divide the first image into a bone region, a soft tissue region, and an air region for each of a bone, a soft tissue, and air, respectively.

17. The dual-energy X-ray imaging apparatus of claim 16, wherein the processor sets the amount of the second X-ray using a respective brightness of each of the divided regions.

18. The dual-energy X-ray imaging apparatus of claim 16, wherein the processor generates a dual-energy image from the first and second images by removing at least one of an X-ray absorption effect of the bone and an X-ray absorption effect of the soft tissue from the first image and the second image using a difference in attenuation characteristics of the first and second X-rays between the bone and the soft tissue.

19. The dual-energy X-ray imaging apparatus of claim 14, wherein the processor sets the determined energy value to maximize a difference in attenuation coefficients between a bone and the soft tissue and minimizes energy absorption of the soft tissue.

20. The dual-energy X-ray imaging apparatus of claim 14, wherein the processor sets the determined energy value, which maximizes a difference in an attenuation coefficient between a bone and the soft tissue, minimizes energy absorption of the soft tissue, and satisfies:

$$wI_T(\overline{E_2}) = I_T(\overline{E_2}) \rightarrow wI_A e^{-\mu T(\overline{E_2})T_T} = I_T(\overline{E_1}),$$

wherein w represents a weight of a power value associated with the X-ray generating unit, $I_T(\overline{E_1})$ represents the brightness of the soft tissue region of the first image, $I_T(\overline{E_2})$ represents the brightness of the soft tissue region of the second image, $\overline{E_1}$ represents an average energy of a spectrum of the first X-ray, and $\overline{E_2}$ represents an average energy of a spectrum of the second X-ray, $\mu T$ represents the attenuation coefficient of the soft tissue, $T_T$ represents a thickness of the soft tissue, $(I_A)$ is a representative brightness for Air (I=brightness, A=Air).

* * * * *

UNITED STATES PATENT AND TRADEMARK OFFICE
CERTIFICATE OF CORRECTION

PATENT NO.        : 9,131,912 B2
APPLICATION NO.   : 13/548555
DATED             : September 15, 2015
INVENTOR(S)       : Cho It is certified that error appears in the above-identified patent and that said Letters Patent is hereby corrected as shown below:

In the claims

Column 16, Claim 5, Line 12 should read

-- $\cdots\ wI_T(\overline{E_2}) = I_T(\overline{E_1}) \rightarrow wI_A e^{-\mu_T(\overline{E_2})l_T} = I_T(\overline{E_1}),\ \cdots$ --

Column 17, Claim 12, Line 14 should read

-- $\cdots\ wI_T(\overline{E_2}) = I_T(\overline{E_1}) \rightarrow wI_A e^{-\mu_T(\overline{E_2})l_T} = I_T(\overline{E_1}),\ \cdots$ --

Column 18, Claim 20, Line 36 should read

-- $\cdots\ wI_T(\overline{E_2}) = I_T(\overline{E_1}) \rightarrow wI_A e^{-\mu_T(\overline{E_2})l_T} = I_T(\overline{E_1}),\ \cdots$ --

Signed and Sealed this
Twenty-fourth Day of May, 2016

Michelle K. Lee
*Director of the United States Patent and Trademark Office*